United States Patent
Byrnes

(10) Patent No.: US 10,098,669 B2
(45) Date of Patent: Oct. 16, 2018

(54) POLYAXIAL BONE SCREW AND BUSHING

(71) Applicant: Alphatec Spine, Inc., Carlsbad, CA (US)

(72) Inventor: Robert Byrnes, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 19 days.

(21) Appl. No.: 14/883,408

(22) Filed: Oct. 14, 2015

(65) Prior Publication Data

US 2017/0105766 A1  Apr. 20, 2017

(51) Int. Cl.
 *A61B 17/70* (2006.01)

(52) U.S. Cl.
 CPC ................ *A61B 17/7037* (2013.01)

(58) Field of Classification Search
 CPC ............ A61B 17/7037; A61B 17/7032; A61B 17/7035; A61B 17/7038
 See application file for complete search history.

(56) References Cited

U.S. PATENT DOCUMENTS

| | | | |
|---|---|---|---|
| 5,443,467 A | 8/1995 | Biedermann | |
| 5,672,176 A | 9/1997 | Biedermann | |
| 6,077,262 A | 6/2000 | Schlapfer | |
| 6,440,137 B1 | 8/2002 | Horvath | |
| 6,837,889 B2 | 1/2005 | Schluzas | |
| 7,377,923 B2 | 5/2008 | Purcell | |
| 8,328,850 B2 * | 12/2012 | Bernard | A61B 17/7032 606/264 |
| 2013/0072981 A1 * | 3/2013 | Jackson | A61B 17/7037 606/263 |
| 2015/0297266 A1 * | 10/2015 | Kirschman | A61B 17/7032 606/266 |
| 2016/0143665 A1 * | 5/2016 | Biedermann | A61B 17/7002 606/267 |

* cited by examiner

*Primary Examiner* — Jacqueline Johanas
(74) *Attorney, Agent, or Firm* — Honigman Miller Schwartz and Cohn LLP

(57) ABSTRACT

A polyaxial screw assembly having a threaded shaft, a rod receiver, a bushing, and a deformable tab is provided. The rod receiver includes a side wall forming a proximal end with an interior portion configured to receive a spinal rod and a distal end configured to receive the spherical head. The bushing is disposed between the spherical head and the sidewall of the rod receiver is configured to engage the spinal rod. The deformable tab is within one of the rod receiver and the bushing and engages with the other of the rod receiver and the bushing. The deformable tab may be disposed within the side wall of the bushing. The deformable tab may be configured to apply an axial force along a longitudinal axis of the threaded shaft to increase a friction force between the rod receiver, the bushing, and the spherical head.

9 Claims, 4 Drawing Sheets

POLYAXIAL BONE SCREW AND BUSHING

FIELD

The invention generally relates to spinal surgery and more particularly to screws and bushings.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

Generally the correct curvature is obtained by manipulating the vertebrae into their proper position and securing that position with a rigid system of screws, rods, intervertebral spaces, and/or plates. The various components of the system may be surgically inserted through open or minimally invasive surgeries. The components may also be inserted through various approaches to the spine including anterior, lateral, and posterior approaches and others in between.

Spinal fixation systems may be used in surgery to align, adjust, and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae. The size, length, and shape of the cylindrical rod depend on the size, number, and position of the vertebrae to be held in a desired spatial relationship relative to each other by the apparatus.

Some vertebral anchors, such as polyaxial pedicle screws, may include a threaded shaft and spherical head, a polyaxial rod receiver, and a bushing disposed between the spherical head and the rod receiver. The bushing may provide a friction fit between the spherical head and the rod receiver as a set screw is threaded into the rod receiver to secure the spinal rod. The bushing may include various features that interact with an anterior portion of the rod receiver to retain the bushing therein. During assembly, it may be desirable to preload the bushing the rod receiver such that some amount of friction force is generated. In this way, the polyaxial rod receiver may be set at a desired angle relative to the threaded shaft once inserted into the vertebrae to ease insertion of the spinal rod or additional instruments as needed.

SUMMARY

A polyaxial screw assembly is provided and includes a threaded shaft, a rod receiver, a bushing, and a deformable tab. The threaded shaft includes a proximal end with a spherical head. The rod receiver includes a side wall forming a proximal end with an interior portion configured to receive a spinal rod and a distal end configured to receive the spherical head. The bushing is disposed between the spherical head and the sidewall of the rod receiver is configured to engage the spinal rod. The deformable tab is within one of the rod receiver and the bushing and engages with the other of the rod receiver and the bushing.

In some features, the deformable tab is in the sidewall of the rod receiver. In other features, the deformable tab is in a sidewall of the bushing. The deformable tab applies a preload condition to wedge a portion of the bushing between the sidewall and the spherical head to increase a friction force therebetween.

In some features, the polyaxial screw assembly further includes a cavity within a sidewall of the bushing. In other features, the polyaxial screw assembly further includes a cavity within a sidewall of the rod receiver.

In yet other features, the deformable tab includes two or more cuts extending completely through one of the rod receiver and the bushing to form a living hinge. The deformable tab retains the bushing within the rod receiver.

In still other features.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Figure 1:
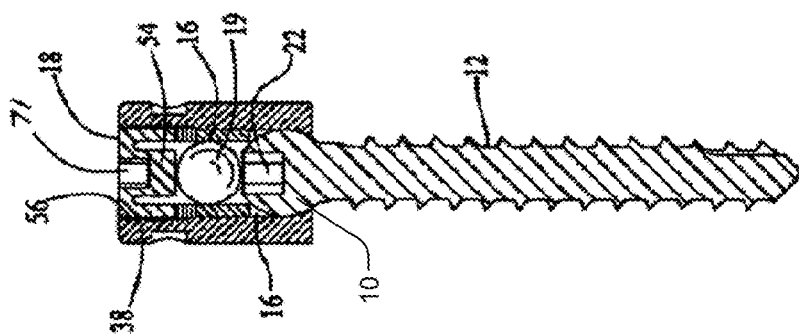
FIG. 1 is perspective view of an exemplary conventional polyaxial pedicle screw including a threaded shaft, polyaxial rod receiver, and bushing shown with a spinal rod and set screw.
Figure 2A:
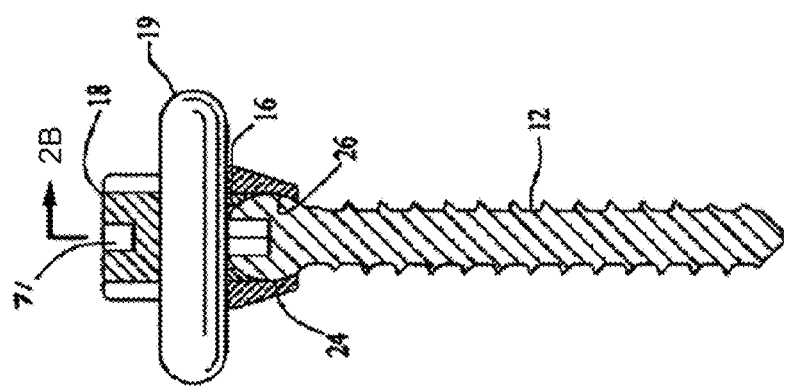
FIG. 2A is a cross-sectional view of FIG. 1 taken along line 2A-2A.
Figure 2B:
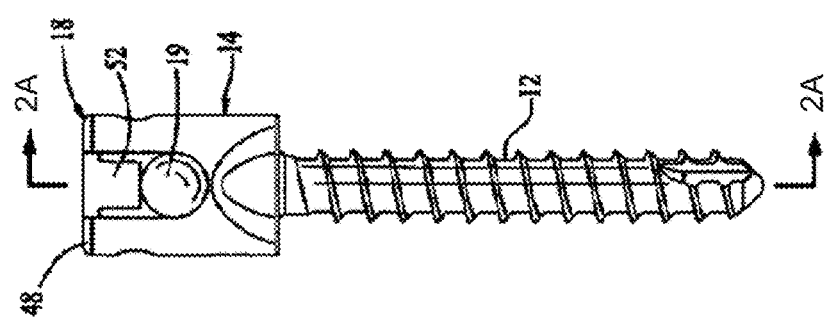
FIG. 2B is a cross-sectional view of FIG. 2A taken along line 2B-2B.

Illustrated in FIGS. 1, 2A, and 2B, a prior art polyaxial screw assembly includes a spherical head 10, a threaded shaft 12, a rod receiver 14, and a bushing 16. The bushing 16 is disposed between the spherical head 10 and an interior portion of the rod receiver 14 that also receives a set screw 18 and a spinal rod 19. The bushing 16 may be forced distally into the rod receiver 14 as the set screw 18 advances and pushes the spinal rod 19 distally.

Figures 3A, 3B:
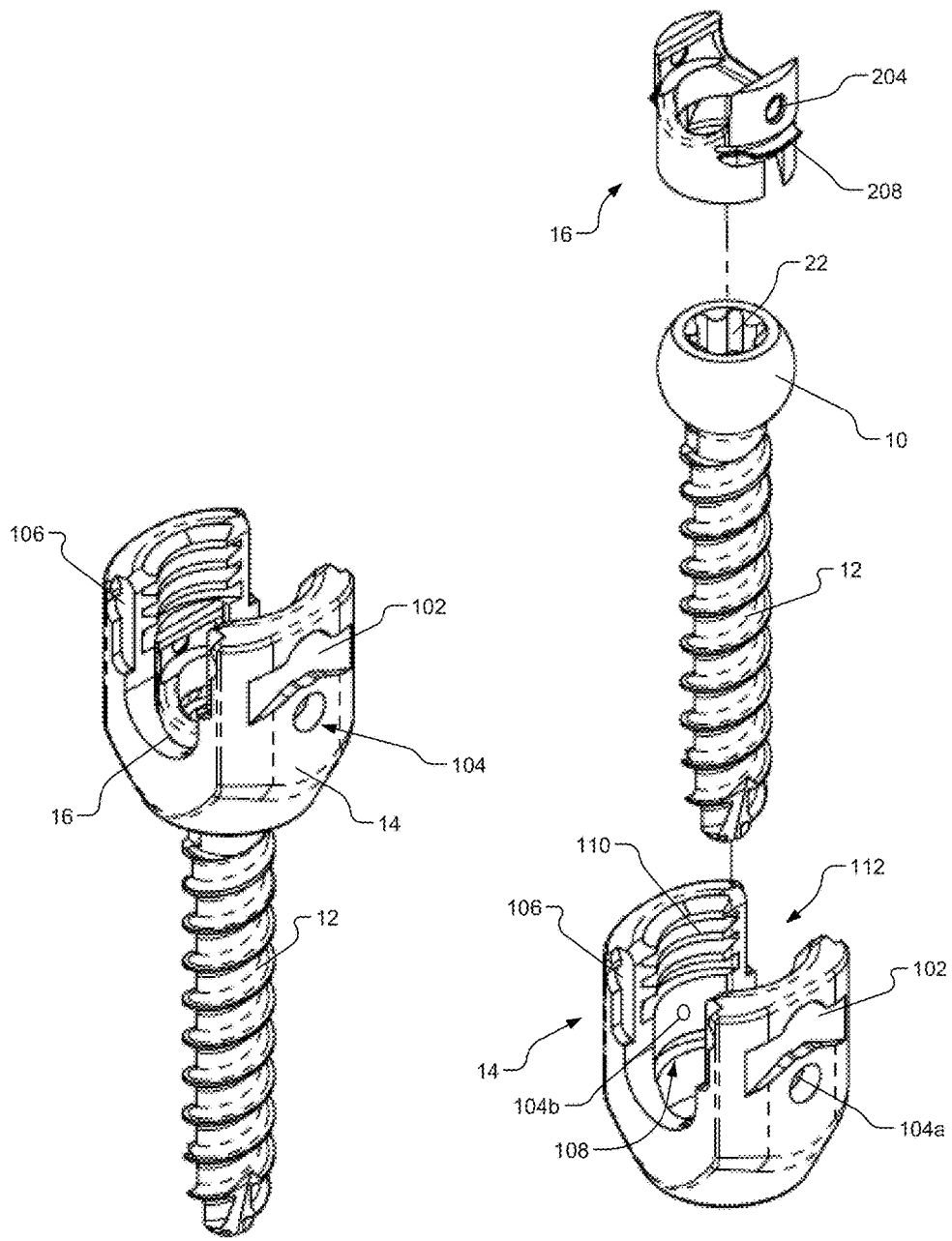
FIG. 3A is a perspective view of an exemplary polyaxial pedicle screw according to one or more embodiments described and illustrated herein.
FIG. 3B is an exploded view of the polyaxial pedicle screw shown in FIG. 3A.

Referring now to FIGS. 3A and 3B, an exemplary polyaxial screw assembly is shown with like numerals representing like features. The rod receiver 14 includes additional features such as attachment points 102 and 106 in its sidewall for attachment of one or more instruments. An interior portion 112 formed by the sidewalls of the rod receiver 14 to receive the bushing 16. The interior face of the sidewalls may include a radial slot 108 at a distal end and a threaded portion 110 at a proximal end.

A dimple 104 may be formed in the exterior of the rod receiver 14 by cold-working or other machining processes. Forming the dimple 104 may create a recessed portion 104a in the exterior surface. Displacement of the material due to the recessed portion 104a in the sidewall may cause a projecting portion 104b on the interior surface of the sidewall to extend inwardly into the inner portion 112. The bushing 16 includes a matching divot 204 intended to mate with the projecting portion 104b. For example, the bushing 16 may be inserted into the interior portion 112 of the rod receiver 14 prior to forming the dimple 104. Once aligned, the dimple 104 may be stamped or otherwise punched to create the recessed portion 104a which subsequently pushes material inward to form the projecting portion 104b to extend into the divot 204. In this manner, the bushing 16 may be locked inside the rod receiver 14. The bushing 16 may also be preloaded against the spherical head 10.

Figure 4A:
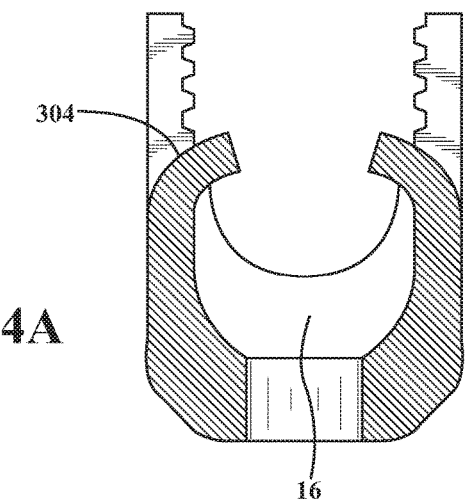
FIG. 4A illustrates a first exemplary interface between a polyaxial rod receiver and a bushing according to the principles of the present disclosure.
Figure 4B:
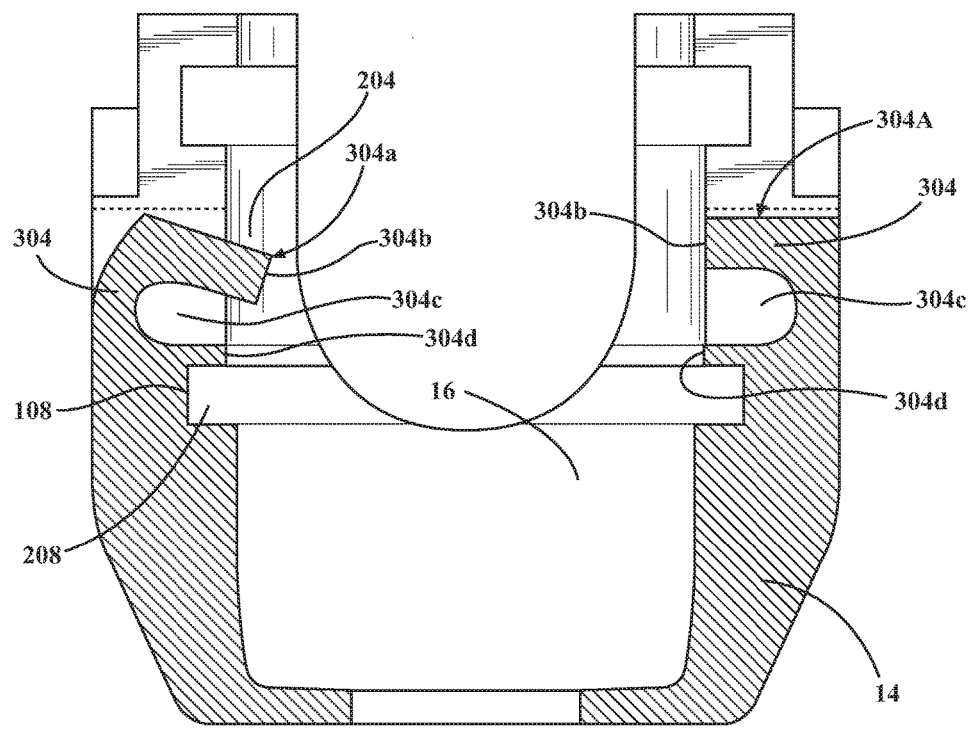
FIG. 4B illustrates a second exemplary interface between a polyaxial rod receiver and a bushing according to the principles of the present disclosure.

Referring now to FIGS. 4A and 4B, another exemplary rod receiver 14 and bushing 16 interface is illustrated utilizing plastically deformable tabs 304 within the sidewall of the rod receiver 14. The tabs 304 may be bent radially inward to engage mating holes or cavities 204 in the bushing 16. Thus, the tabs 304 may be created by cutting out two or more sides from the sidewall of the rod receiver 14 to permit flexing of the tab 304. For a rectangular tab, two longitudinal cuts and one lateral cut may be used in conjunction with chamfering or removal of additional material to result in the desired amount of plastic deformation. FIG. 4A illustrates a rod receiver 14 wherein the tab 304 is a generally elongated member. FIG. 4B illustrates an embodiment wherein the tab 304 is a U-shaped member. In particular, the tab 304 includes a top portion 304a having a distal edge 304b. The top portion 304a is a generally planar member. A radiused groove 304c is disposed beneath the top portion 304a and a lower lip 304d is disposed beneath the top portion 304a with the radiused groove 304c disposed between the top portion 304a and the lower lip 304d so as to form the U-shape. The deformable tab is movable between a rest position and an engaged position. With reference again to FIG. 4B and also to FIG. 3A, the bushing 16 includes a radial edge 208 which is seated within the radial slot 108 of the receiver 14. For illustrative purpose, FIG 4B shows the deformable tab 304 in both the rest position and the engaged position. In particular, the deformable tab 304a on the left hand side of FIG. 4B is in the engaged position and the deformable tab 304 on the right hand side of FIG. 4B is in the rest position. In the engaged position the radial edge 208 of the bushing is seated within the radial slot 108, wherein the deformable tab 304 is actuated so as to press the distal edge 304b of the top portion 304a of the deformable tab into engagement with the bushing 16. The deformable tab on the right hand side of FIG. 4B is in the rest position wherein the distal edge 304b of the top portion 304a is flush with the interior portion of the side wall of the receiver 14. It should be appreciated that in the rest position, the bushing 16 is not seated within the receiver 14.

Figure 5A:
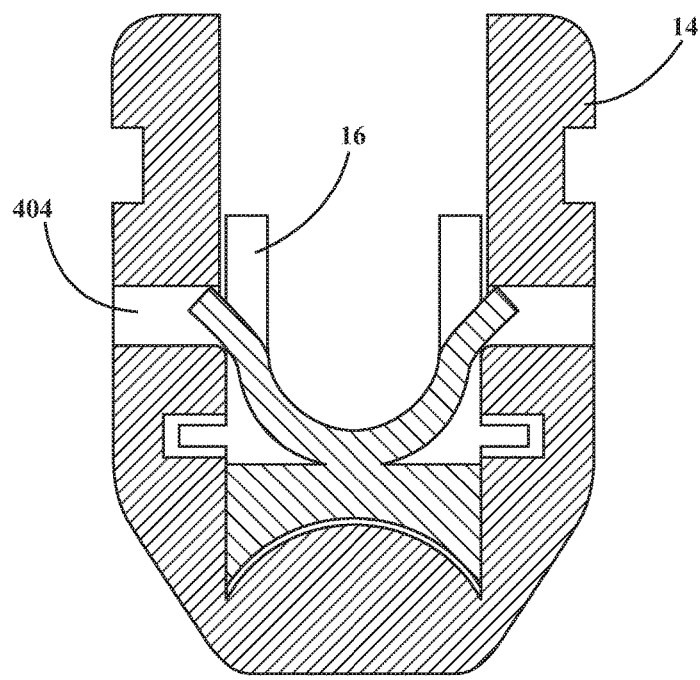
FIG. 5A illustrates another exemplary rod receiver and bushing interface utilizing plastically deformable tabs within the sidewall of the bushing.
Figures 5B, 5C:
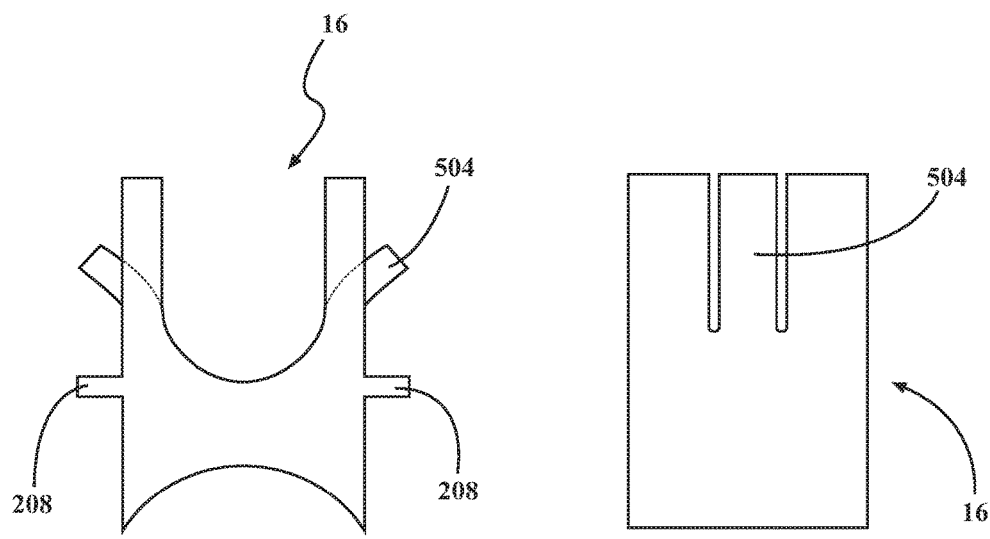
FIG. 5B is an isolated view of the bushing showing the tabs.
FIG. 5C illustrates the bushing having cuts to form the tab shown in FIG. 5B.

Referring to FIGS. 5A, 5B and 5C, another exemplary rod receiver 14 and bushing interface 16 is illustrated utilizing plastically deformable tabs 504 within the sidewall of the bushing 16. The tabs 504 may be bent radially outward to engage mating holes or cavities 404 in the rod receiver 14. Thus, the tabs 504 may be created by cutting out two or more sides from the sidewall of the bushing 16 to permit flexing of the tab 504. For a rectangular tab, two longitudinal cuts and one lateral cut may be used in conjunction with chamfering or removal of additional material to result in the desired about of plastic deformation.

In other examples of the invention, no cavity may be provided to receive the tabs 304 or 505. That is, referring back to FIGS. 4A and 4B, the tabs 304 of the rod receiver 14 may deform radially inward and engage with an outer surface of the sidewall portion of the bushing 16. The tabs 304 may frictionally engage with the outer surface to retain the bushing 16. In addition, by adjusting the amount of force applied to bend the tabs 304, a downward force may act on the bushing 16 to increase the frictional force between the bushing 16, the rod receiver 14, and the spherical head 10 of the screw. In FIGS. 5A-5C, the tabs 504 of the bushing 16 may deform radially outward and engage an inner surface of the sidewall portion of the rod receiver 14. The tabs 504 may frictionally engage the inner surface to retain the bushing 16. Likewise, adjusting the amount of force applied to bend the tabs 504, downward force may act on the bushing 16 to increase the frictional force between the bushing 16, the rod receiver 14, and the spherical head 10 of the screw.

The invention claimed is:

1. A polyaxial screw assembly, comprising:
   a threaded shaft including a proximal end with a spherical head;
   a rod receiver including a side wall forming a proximal end with an interior portion configured to receive a spinal rod and a distal end configured to receive the spherical head, a radial slot adjacent the distal end;

a bushing disposed between the spherical head and the sidewall of the rod receiver configured to engage the spinal rod, the bushing having a radial edge configured to be seated in the radial slot; and a deformable tab within the rod receiver, the deformable tab movable between a rest position and an engaged position, the deformable tab having a top portion with a distal edge, a lower lip spaced apart from the top portion so as to define a radiused groove between the top portion and the lower lip and giving the deformable tab a generally "U" shaped cross-section, the lower lip spaced apart from the radial slot so as to be disposed between the radial slot and the top portion, wherein in the rest position the distal edge of the top portion of the deformable tab is flush with the interior portion of the side wall, and wherein in the engaged position the top portion is pressed into engagement with the bushing and the radial edge of the bushing is seated within the radial slot of the rod receiver.

2. The polyaxial screw assembly of claim 1, wherein the deformable tab is in the sidewall of the rod receiver.

3. The polyaxial screw assembly of claim 2, further comprising a cavity within a sidewall of the bushing.

4. The polyaxial screw assembly of claim 1, wherein the deformable tab applies a preload condition to wedge a portion of the bushing between the sidewall and the spherical head to increase a friction force therebetween.

5. The polyaxial screw assembly of claim 1, wherein the deformable tab retains the bushing within the rod receiver.

6. The polyaxial screw assembly of claim 1, wherein the deformable tab is configured to apply an axial force along a longitudinal axis of the threaded shaft to increase a friction force between the rod receiver, the bushing, and the spherical head.

7. A polyaxial screw assembly, comprising:

a threaded shaft including a proximal end with a spherical head; a rod receiver including a side wall forming a proximal end with an interior portion configured to receive a spinal rod and a distal end configured to receive the spherical head, a radial slot adjacent the distal end;

a bushing disposed between the spherical head and the sidewall of the rod receiver configured to engage the spinal rod, the bushing having a radial edge configured to be seated in the radial slot;

a cavity within a sidewall of the bushing; and a deformable tab within the rod receiver, the deformable tab movable between a rest position and a engaged position, the deformable tab having a top portion with a distal edge, a lower lip spaced apart from the top portion so as to define a radiused groove between the top portion and the lower lip and giving the deformable tab a generally "U" shaped cross-section, the lower lip spaced apart from the radial slot so as to be disposed between the radial slot and the top portion, wherein in the rest position the distal edge of the top portion of the deformable tab is flush with the interior portion of the side wall, and wherein in the engaged position the top portion is pressed into engagement with the bushing and the radial edge of the bushing is seated within the radial slot of the rod receiver.

8. The polyaxial screw assembly of claim 7, wherein the deformable tab applies a preloaded condition to wedge a portion of the bushing between the sidewall and the spherical head to increase a friction force therebetween.

9. The polyaxial screw assembly of claim 7, wherein the deformable tab retains the bushing within the rod receiver.

* * * * *